United States Patent [19]

Ishikura et al.

[11] Patent Number: 5,087,734
[45] Date of Patent: Feb. 11, 1992

[54] CRYSTAL MODIFICATION OF MAGNESIUM SALT OF MONO-P-NITROBENZYL MALONATE AND PROCESS FOR PRODUCING THE SAME

[75] Inventors: Tsukasa Ishikura, Fukuyama; Shigeru Matsuyama, Kita, both of Japan

[73] Assignee: Nippon Kayaku Kabushiki Kaisha, Tokyo, Japan

[21] Appl. No.: 512,759

[22] Filed: Apr. 20, 1990

[30] Foreign Application Priority Data

Apr. 26, 1989 [JP] Japan .................................. 1-104717

[51] Int. Cl.$^5$ ..................... C07C 69/38; C07C 67/297
[52] U.S. Cl. ..................................... 560/193; 562/590
[58] Field of Search ........................ 560/193; 562/590

[56] References Cited

U.S. PATENT DOCUMENTS 4,786,427 11/1988 Dare-Edwards ............... 560/193 X

*Primary Examiner*—Jose G. Dees
*Assistant Examiner*—Vera C. Clarke
*Attorney, Agent, or Firm*—Nields & Lemack

[57] ABSTRACT

The present invention provides a crystal modification of magnesium salt of mono-p-nitrobenzyl malonate (hereinunder referred to as "$\beta$-type crystal") which is characterized by an X-ray diffraction pattern having strong peaks at angles of diffraction of ($2\theta$) [°] 4.5, 8.9 and 13.3 according to X-ray diffractometry with Cu-K$\alpha$ line, and a process for producing the $\beta$-type crystal modification of magnesium salt of mono-p-nitrobenzyl malonate comprising the step of reacting a water-soluble magnesium salt with an alkali metal salt or ammonium salt of mono-p-nitrobenzyl malonate. This process facilitates the production of the $\beta$-type crystal modification having a higher purity than a known $\alpha$-type crystal modification. The $\beta$-type crystal is a very useful intermediate as a starting material of pharmaceutical.

4 Claims, 2 Drawing Sheets

CRYSTAL MODIFICATION OF MAGNESIUM SALT OF MONO-P-NITROBENZYL MALONATE AND PROCESS FOR PRODUCING THE SAME

BACKGROUND OF THE INVENTION

The present invention relates to a crystal modification of magnesium salt of mono-p-nitrobenzyl malonate and a process for producing the same.

Magnesium salt of mono-p-nitrobenzyl malonate is an important intermediate as a starting material of pharmaceuticals.

Magnesium salt of mono-p-nitrobenzyl malonate cannot be obtained by merely adding magnesium hydroxide to mono-p-nitrobenzyl malonate.

As conventional methods of producing magnesium salt of mono-p-nitrobenzyl malonate, the method of reacting mono-p-nitrobenzyl malonate with magnesium ethoxide in tetrahydrofuran, and further adding ethyl ether thereto is disclosed in, for example, Japanese Patent Application Laid-Open (KOKAI) Nos. 57-159761 (1982) and 58-208292 (1983). This method, however, has problems as far as manufacturing is concerned that magnesium ethoxide is expensive and that a special solvent such as tetrahydrofuran and ethyl ether is necessary. The crystal obtained by the conventional method is a crystal modification of magnesium salt of mono-p-nitrobenzyl malonate (hereinunder referred to as "α-type crystal", see FIG. 1) which is characterized by an X-ray diffraction pattern having strong peaks at angles of diffraction of ($2\theta$) [°] 5.6 and 16.3 according to X-ray diffractometry with Cu-K$\alpha$ line, and is liable to contain impurities such as by-produced ethyl p-nitrobenzyl malonate, thereby making purification difficult.

As described above, the conventional method has problems such as the use of an expensive material, necessity for a special solvent and difficulty in adequate purification of a crystal modification obtained.

Accordingly, development of an industrial manufacturing method and a crystalline modification free from the above-described problems is demanded.

As a result of studies undertaken by the present inventors so as to eliminate these problems, the present invention has been achieved.

SUMMARY OF THE INVENTION

The present invention provides a crystal modification of magnesium salt of mono-p-nitrobenzyl malonate (hereinunder referred to as "β-type crystal") which is characterized by an X-ray diffraction pattern having strong peaks at angles of diffraction of ($2\theta$) [°] 4.5, 8.9 and 13.3 according to X-ray diffractometry with Cu-K$\alpha$ line, and a process for producing the β-type crystal modification of magnesium salt of mono-p-nitrobenzyl malonate comprising the step of reacting a water-soluble magnesium salt with an alkali metal salt or ammonium salt of mono-p-nitrobenzyl malonate. (An error of about ±0.5° is generally allowed in the indication of the angle of X-ray diffraction).

The β-type crystal modification of magnesium salt of mono-p-nitrobenzyl malonate according to the present invention is produced by a simple process which does not require an organic solvent or other expensive reagents and diminishes the possibility of containing impurities.

DETAILED DESCRIPTION OF THE INVENTION

Figure 1:
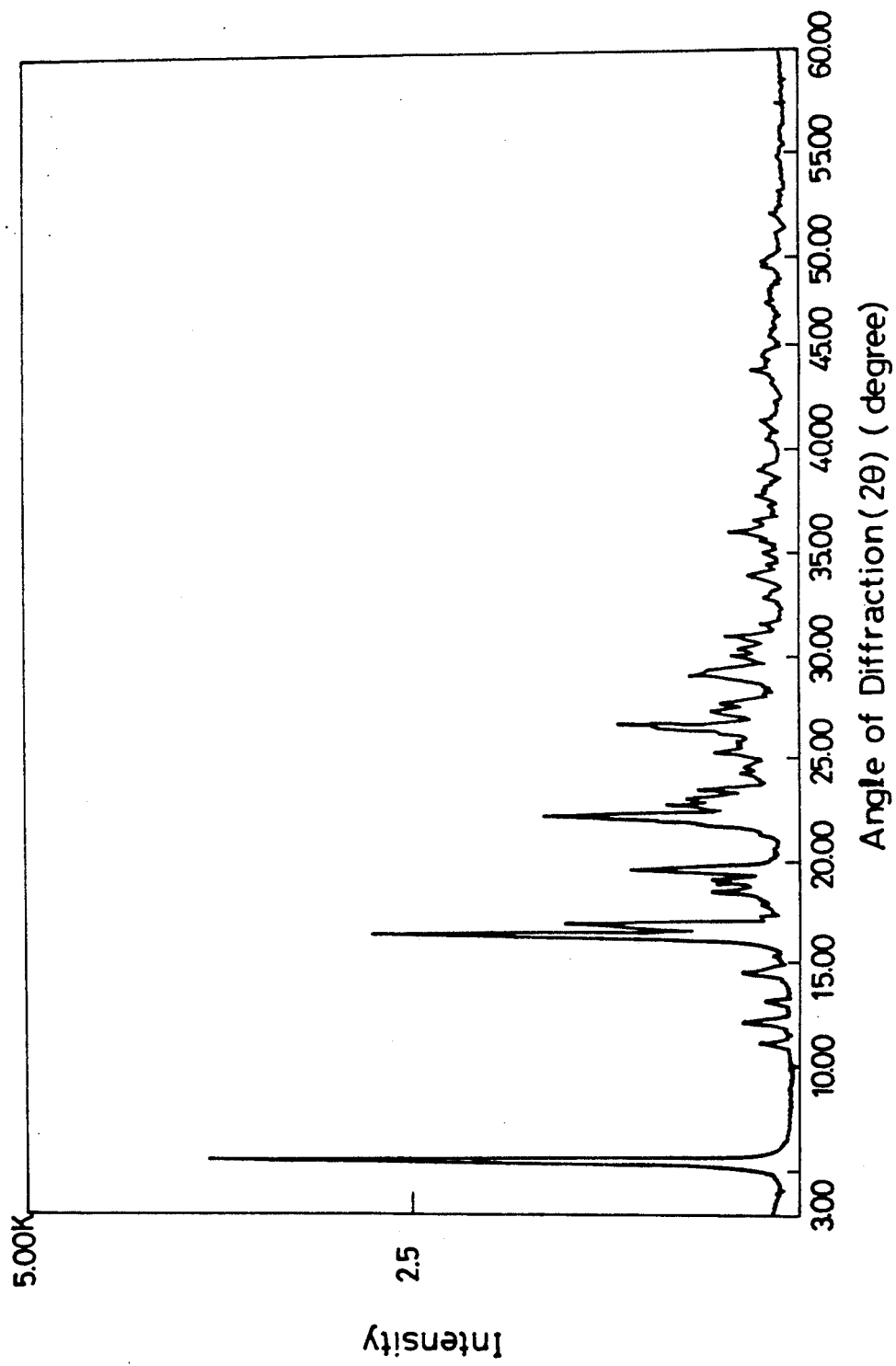
FIG. 1 is an X-ray diffraction pattern of a known α-type crystal modification of magnesium salt of mono-p-nitrobenzyl malonate.

The present invention is explained in more detail. In the process of the present invention, an alkali metal salt or ammonium salt of mono-p-nitrobenzyl malonate is used as the starting material. Examples thereof include a lithium salt, sodium salt, potassium salt and ammonium salt of mono-p-nitrobenzyl malonate. Mono-p-nitrobenzyl malonate can be obtained by the reaction between a p-nitrobenzyl alcohol and Meldrum's acid, for example, in accordance with a method described in Japanese Patent Application Laid-Open (KOKAI) No. 57-159761 (1982).

Mono-p-nitrobenzyl malonate can also be obtained by reacting p-nitrobenzyl alcohol with malonic acid in an organic solvent such as toluene, xylene in the presence of acid such as p-toluenesulfonic acid.

An alkali metal salt or ammonium salt of mono-p-nitrobenzyl malonate can be obtained, for example, by reacting mono-p-nitrobenzyl malonate with an alkali hydroxide such as LiOH, NaOH and KOH, an alkali metal salt of a weak acid such as $Li_2CO_3$, $LiHCO_3$, $Na_2CO_3$, $NaHCO_3$, $K_2CO_3$ and $KHCO_3$, ammonia, or an ammonium salt of a weak acid such as $(NH_4)_2CO_3$ preferably in water preferably at a reaction temperature of $-10°$ to $90°$ C., more preferably at $0°$ to $50°$ C. In this case, the amount of the alkali hydroxide, alkali metal salt of a weak acid, ammonia or ammonium salt of a weak acid used is 1.0 to 1.2 equivalents based on 1 mol of mono-p-nitrobenzyl malonate. The alkali metal salt or ammonium salt of mono-p-nitrobenzyl malonate may be isolated but ordinarily it is used for the next reaction as it is without being isolated.

In the process of the present invention, the preferable reaction solvent is water, but may be a mixture of water with an alcohol, ether, aliphatic hydrocarbon, aromatic hydrocarbon or the like.

As a water-soluble magnesium salt, magnesium halides such as magnesium chloride, magnesium bromide and magnesium iodide, magnesium nitrate and magnesium sulfide are used. These may be preferably used in the form of an aqueous solution. In the reaction of the alkali metal salt or ammonium salt of mono-p-nitrobenzyl malonate and the water-soluble magnesium salt, it is preferred that an aqueous solution of the water-soluble magnesium salt is added to an aqueous solution of the alkali metal salt or ammonium salt of mono-p-nitrobenzyl malonate. The amount of the water-soluble magnesium salt preferably used is 0.8 to 4.0 times, more preferably 0.9 to 3.0 times the stoichiometric amount. The reaction temperature is ordinarily $-10°$ to $90°$ C., preferably $0°$ to $50°$ C. The time required for reaction is ordinarily 10 minutes to 10 hours.

The magnesium salt of mono-p-nitrobenzyl malonate (β-type crystal) can be isolated by, for example, filtration. The purity of the β-type crystal can be easily measured by liquid chromatography (L.C.)

According to the process of the present invention, it is possible to produce a novel crystal modification (β- type) of magnesium salt of mono-p-nitrobenzyl malonate by reacting a water-soluble magnesium salt with an alkali metal salt or ammonium salt of mono-p-nitrobenzyl malonate. This novel crystal modification is one which has little possibility of containing impurities.

The present invention is explained in furthermore detail with reference to the following examples.

EXAMPLE 1

To a mixture of 23.9 g of mono-p-nitrobenzyl malonate and 100 g of water, 37.4 g of 15% KOH aqueous solution was added dropwise at 20° to 30° C. over a period of 30 minutes to obtain an aqueous solution of potassium salt of mono-p-nitrobenzyl malonate. Thereafter, 40 g of 12% magnesium chloride aqueous solution was added dropwise at 20° to 30° C. over a period of 1 hour and the mixture was further stirred for 30 minutes. The product was filtered off, washed with water and dried to obtain 22.8 g of magnesium salt (dihydrate) of mono-p-nitrobenzyl malonate (yield: 85%, purity: 99.5%).

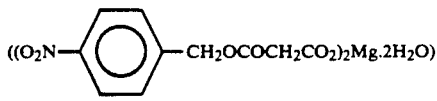

Analysis: Mg content (Atomic absorption spectrometry) 4.5% (calculated), 4.6% (found).

Moisture (K.F. method) 6.7% (calculated), 6.8% (found).

Figure 2:
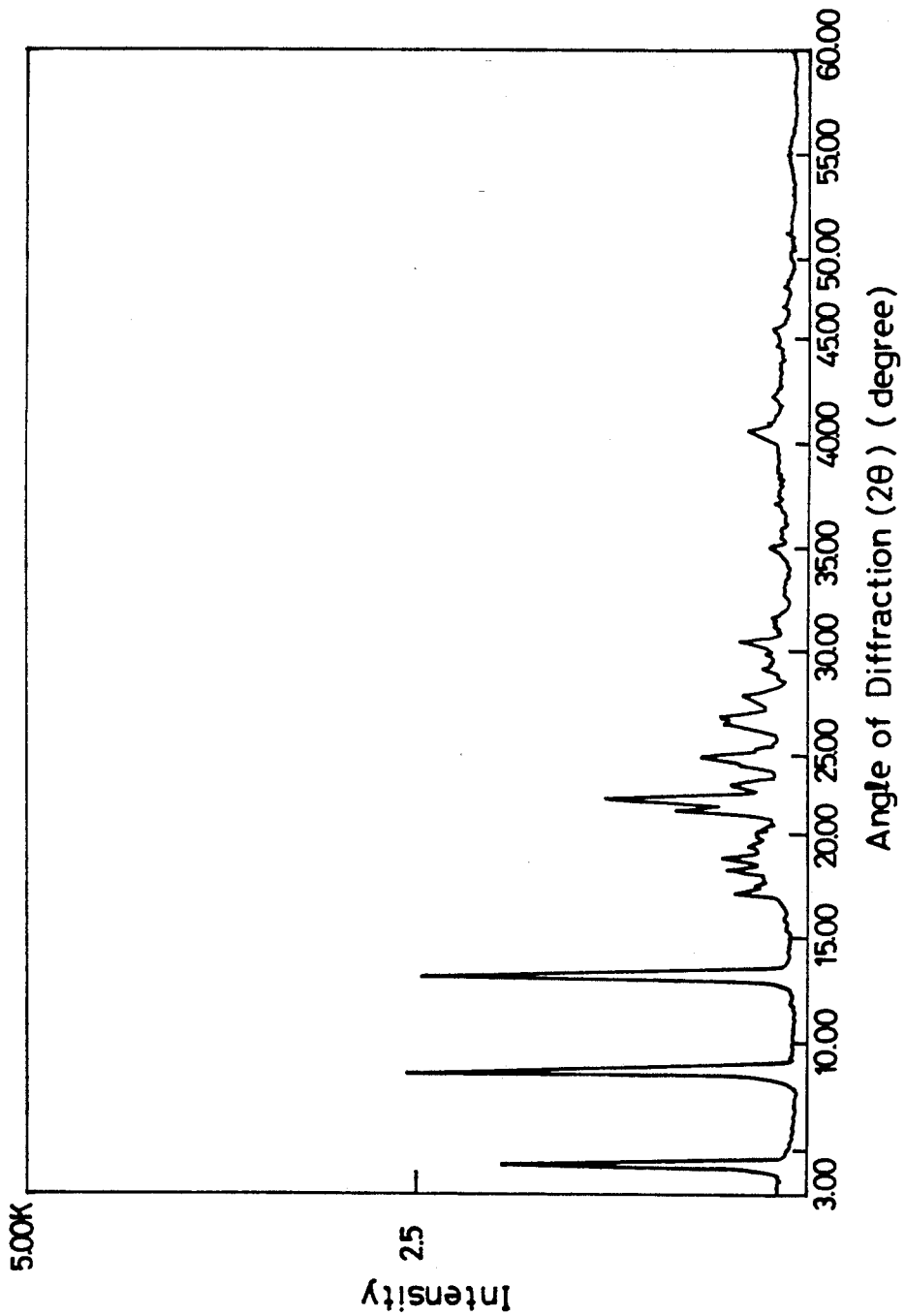
FIG. 2 is an X-ray diffraction pattern of the β-type crystal modification of magnesium salt of mono-p-nitrobenzyl malonate according to the present invention.

As is clear from the X-ray diffraction pattern of the product shown in FIG. 2, it shows the β-type crystal modification having strong peaks at angles of diffraction of (2θ) [°] 4.5, 8.9 and 13.3.

EXAMPLE 2

To a mixture of 23.9 g of mono-p-nitrobenzyl malonate and 200 g of water, 5.0 g of aqueous 30% ammonia water was added dropwise at 20° to 30° C. over a period of 30 minutes to obtain an aqueous solution of ammonium salt of mono-p-nitrobenzyl malonate. Thereafter, 46 g of 20% magnesium bromide aqueous solution was added dropwise at 20° to 30° C. over a period of 1 hour and the mixture was further stirred for 1 hour. The product was filtered off, washed with water and dried, thereby obtaining 21.3 g of a magnesium salt (dihydrate) of mono-p-nitrobenzyl malonate (yield: 79%, purity: 98.2%).

The crystal showed the same β-type crystal modification as that obtained in Example 1.

EXAMPLE 3

To a mixture of 23.9 g of mono-p-nitrobenzyl malonate and 500 g of water, 5.3 g of sodium carbonate was added at 20° to 30° C. over a period of 30 minutes and the mixture was stirred for 1 hour to obtain an aqueous solution of sodium salt of mono-p-nitrobenzyl malonate. Thereafter, 30 g of aqueous 2.0% magnesium sulfate solution was added dropwise at 20° to 30° C. over a period of 1 hour. Thereafter, in the same way as in Example 1, 20.8 g of magnesium salt (dihydrate) of mono-p-nitrobenzyl malonate was obtained (yield: 78%, purity: 97.2%).

The crystal showed the same β-type crystal modification as that obtained in Example 1.

EXAMPLE 4 a) Preparation of mono-p-nitrobenzyl malonate by esterification of malonic acid with p-nitrobenzyl alcohol:

A mixture of 27.5 g of p-nitrobenzyl alcohol, 28.1 g of malonic acid, 0.4 g of p-toluene sulfonic acid and 180 ml of toluene was heated to reflux (from 100° to 115° C.) for 6 hours in a 300 ml flask. During this period, the water formed was separated as the toluene azeotrope. The reaction mixture was cooled to room temperature, and thus formed precipitates were collected by filtration, washed with toluene and dried to give 48 g of crude mono-p-nitrobenzyl malonate (crude yield: 59%, purity: 52.9%)

b) To a stirred suspension of 48 g of crude mono-p-nitrobenzyl malonate obtained above in water (240 g) was added dropwise 127.2 g of aqueous 15% $K_2CO_3$ solution at 20° to 30° C. over a period of 1 hour until a neutral suspension was obtained. After stirring for 1 hour insoluble compounds were removed by filtration and washed with water. The filtrates and washings were containing 28.8 g of potassium salt of mono-p-nitrobenzyl malonate. To combined solution of the filtrates and washings was added dropwise 87.7 g of aqueous 15% magnesium chloride solution at 20° to 25° C. over a period of 1 hour, and stirring was continued for 2 hours. Thus formed precipitates were collected by filtration, washed with water and dried to give 24.8 g of magnesium salt (dihydrate) of mono-p-nitrobenzyl malonate (yield: 89%, purity: 99.3%).

The crystal showed the same β-type crystal modification as that obtained in Example 1.

What is claimed is:

1. A crystal modification of magnesium salt of mono-p-nitrobenzyl malonate which is characterized by an X-ray diffraction pattern having strong peaks at angles of diffraction of (2θ) [°] 4.5, 8.9 and 13.3 according to X-ray diffractometry with Cu-Kα line.

2. A process for producing the crystal modification of magnesium salt of mono-p-nitrobenzyl malonate according to claim 1, which comprises the step of reacting a water-soluble magnesium salt with an alkali metal salt or ammonium salt of mono-p-nitrobenzyl malonate.

3. A process according to claim 2, wherein said reaction is carried out in water at a temperature of −10° to 90° C.

4. A process according to claim 2, wherein 0.8 to 4.0 times the stoichiometric amount of the water-soluble magnesium salt is reacted with the alkali metal salt or ammonium salt of mono-p-nitrobenzyl malonate.

* * * * *